(12) United States Patent
Venkataraman et al.

(10) Patent No.: US 12,189,821 B2
(45) Date of Patent: *Jan. 7, 2025

(54) METHOD AND SYSTEM FOR ANONYMIZING RAW SURGICAL PROCEDURE VIDEOS

(71) Applicant: Verb Surgical Inc., Santa Clara, CA (US)

(72) Inventors: Jagadish Venkataraman, Menlo Park, CA (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/320,127

(22) Filed: May 18, 2023

(65) Prior Publication Data

US 2023/0289474 A1    Sep. 14, 2023

Related U.S. Application Data

(63) Continuation of application No. 17/380,909, filed on Jul. 20, 2021, now Pat. No. 11,687,671, which is a
(Continued)

(51) Int. Cl.
*G06F 21/62*    (2013.01)
*A61B 90/00*    (2016.01)
(Continued)

(52) U.S. Cl.
CPC ........ *G06F 21/6254* (2013.01); *A61B 90/361* (2016.02); *H04L 63/0407* (2013.01); *G06F 16/2272* (2019.01); *G16H 40/60* (2018.01)

(58) Field of Classification Search
CPC ............... G06F 21/6254; A61B 90/361; H04L 63/0407
(Continued)

(56) References Cited

U.S. PATENT DOCUMENTS

| 10,679,743 B2 | 6/2020 | Venkataraman |
| 2003/0046562 A1 | 3/2003 | Uchikubo |

(Continued)

FOREIGN PATENT DOCUMENTS

| JP | 2002253478 A | 9/2002 |
| KR | 10-2018-0098869 A | 9/2018 |

(Continued)

OTHER PUBLICATIONS

European Search Report and Search Opinion received for EP Application No. 19929816.7, mailed on May 23, 2023, 9 pages.
(Continued)

*Primary Examiner* — Kambiz Zand
*Assistant Examiner* — Phuc Pham
(74) *Attorney, Agent, or Firm* — Aikin & Gallant, LLP

(57) ABSTRACT

This patent disclosure provides various verification techniques to ensure that anonymized surgical procedure videos are indeed free of any personally-identifiable information (PII). In a particular aspect, a process for verifying that an anonymized surgical procedure video is free of PII is disclosed. This process can begin by receiving a surgical video corresponding to a surgery. The process next removes personally-identifiable information (PII) from the surgical video to generate an anonymized surgical video. Next, the process selects a set of verification video segments from the anonymized surgical procedure video. The process subsequently determines whether each segment in the set of verification video segments is free of PII. If so, the process replaces the surgical video with the anonymized surgical video for storage. If not, the process performs additional PII removal steps on the anonymized surgical video to generate an updated anonymized surgical procedure video.

20 Claims, 4 Drawing Sheets

Related U.S. Application Data continuation of application No. 16/418,809, filed on May 21, 2019, now Pat. No. 11,080,424.

(51) Int. Cl.
*H04L 9/40* (2022.01)
*G06F 16/22* (2019.01)
*G16H 40/60* (2018.01)

(58) Field of Classification Search
USPC .......................................................... 726/26
See application file for complete search history.

(56) References Cited

U.S. PATENT DOCUMENTS

| | | | |
|---|---|---|---|
| 2013/0182006 | A1 | 7/2013 | Syeda-Mahmood et al. |
| 2017/0235880 | A1 | 8/2017 | Wright et al. |
| 2018/0005666 | A1 | 1/2018 | Yang et al. |
| 2018/0110398 | A1* | 4/2018 | Schwartz ............. A61B 1/0002 |
| 2018/0122506 | A1 | 5/2018 | Grantcharov et al. |
| 2018/0211062 | A1 | 7/2018 | Holland et al. |
| 2018/0303343 | A1* | 10/2018 | Dubin ..................... A61B 8/14 |
| 2019/0362834 | A1 | 11/2019 | Venkataraman et al. |
| 2019/0377901 | A1 | 12/2019 | Balzer et al. |
| 2020/0082934 | A1 | 3/2020 | Venkataraman |
| 2020/0273557 | A1 | 8/2020 | Wolf et al. |
| 2020/0285771 | A1* | 9/2020 | Dey .................... G06F 21/6272 |
| 2020/0293679 | A1 | 9/2020 | Handy et al. |

FOREIGN PATENT DOCUMENTS

| | | |
|---|---|---|
| KR | 10-2018-0106243 A | 10/2018 |
| KR | 10-1955025 B1 | 3/2019 |
| WO | 2018/169257 A1 | 9/2018 |

OTHER PUBLICATIONS

International Preliminary Report on Patentability received for PCT Patent Application No. PCT/US19/34064, mailed on Dec. 2, 2021, 7 pages.

International Search Report and Written Opinion received for PCT Patent Application No. PCT/US19/34064, mailed on Feb. 21, 2020, 8 pages.

Non-Final Office Action received for U.S. Appl. No. 16/418,809, mailed on Dec. 8, 2020, 28 pages.

Non-Final Office Action received for U.S. Appl. No. 17/380,909, mailed on Oct. 3, 2022, 39 pages.

Notice of Allowance received for U.S. Appl. No. 16/418,809, mailed on Mar. 31, 2021, 20 pages.

Notice of Allowance received for U.S. Appl. No. 17/380,909, mailed on Feb. 15, 2023, 13 pages.

Office Action received for Korean Patent Application No. 10-2021-7041464, mailed on Mar. 12, 2024, 13 pages (6 pages of English Translation and 7 pages of Original Document).

* cited by examiner

METHOD AND SYSTEM FOR ANONYMIZING RAW SURGICAL PROCEDURE VIDEOS

PRIORITY CLAIM AND RELATED PATENT APPLICATIONS

This patent application is a continuation of, and hereby claims the benefit of priority under 35 U.S.C. § 120 to U.S. patent application Ser. No. 17/380,909, filed on 20 Jul. 2021, entitled "Method and System for Anonymizing Raw Surgical Procedure Videos," which is a continuation of U.S. patent application Ser. No. 16/418,809, filed on 21 May 2019, entitled "Method and System for Anonymizing Raw Surgical Procedure Videos," now U.S. Pat. No. 11,080,424, issued 3 Aug. 2021. The above-listed applications are hereby incorporated by reference as a part of this patent document.

TECHNICAL FIELD

The present disclosure generally relates to building surgical procedure video analysis tools and, more specifically, to systems, devices and techniques for anonymizing raw surgical procedure videos to de-identify personally-identifiable information and providing the anonymized surgical procedure videos for various research purposes.

BACKGROUND

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exist and continue to be created as a result of a large number of surgical cases performed by many different surgeons from different hospitals.

The simple fact of the existence of a huge (and constantly increasing) number of surgical videos of a particular surgical procedure makes processing and analyzing the surgical videos of the given procedure a potential machine learning problem. However, raw surgical videos from recordings in the operating room (OR) can contain all sorts of patient information in the form of text-based identifiers including the patient's name, medical record number, age, sex, demographic, date and time of surgery, among others. Furthermore, some surgical procedure videos can also contain sensitive and personal information captured inside the OR, such as information written on the whiteboard in the OR and the faces of surgical staff. Hence, before raw surgical videos can be used for various research purposes such as for building machine-learning tools, the raw surgical procedure videos need to be anonymized in order to be free of personally-identifiable information and to be compliant with HIPAA regulations and processes.

There are several automatic anonymization tools available for removing text identifiers from files and for detecting and removing sensitive information from medical image files, such as patient's CT scans, X-rays, etc. However, existing techniques for anonymizing sensitive information buried in raw procedure videos are generally manual-based which require human operators to review individual videos to identify the sensitive information in the video frames and then manually anonymized (e.g., by removing or burring out) the sensitive information. Manual-based video anonymizing processes are both labor-intensive and time-consuming. In particular, building machine learning tools requires that a large number of raw surgical procedure videos be first anonymized, which makes manual-based video anonymization impractical for machine learning purposes. Unfortunately, there are no existing automatic anonymization tools for anonymizing sensitive information buried in raw surgical videos.

SUMMARY

This patent disclosure provides various embodiments for anonymizing raw surgical procedure videos recorded by a recording device, such as an endoscope camera, during a surgical procedure performed on a patient inside an operating room (OR). In one aspect, a process for anonymizing raw surgical procedure videos recorded by a recording device within an OR is disclosed. This process can begin by receiving a set of raw surgical videos corresponding to a surgical procedure performed within the OR. The process next merges the set of raw surgical videos to generate a surgical procedure video corresponding to the surgical procedure. Next, the process detects image-based personally-identifiable information embedded in the set of raw video images of the surgical procedure video. When image-based personally-identifiable information is detected, the process automatically de-identifies the detected image-based personally-identifiable information in the surgical procedure video.

This patent disclosure also provides various verification techniques to ensure that anonymized procedure surgical videos are indeed free of any personally-identifiable information (PII). In a particular aspect, a process for verifying that an anonymized surgical procedure video is free of PII is disclosed. This process can begin by receiving a surgical video corresponding to a surgery. The process next removes personally-identifiable information (PII) from the surgical video to generate an anonymized surgical video. Next, the process selects a set of verification video segments from the anonymized surgical procedure video. The process subsequently determines whether each segment in the set of verification video segments is free of PII. If so, the process replaces the surgical video with the anonymized surgical video for storage. If not, the process performs additional PII removal steps on the anonymized surgical video to generate an updated anonymized surgical procedure video.

In some embodiments, the process selects the set of verification video segments from the anonymized surgical video by performing a strategic random-sampling, which includes randomly-selecting the set of verification video segments from one or more time periods in the anonymized surgical video determined to be associated with higher probabilities to contain PII.

In some embodiments, the process performs the strategic random-sampling by: (1) segmenting the anonymized surgical video into a set of video portions including the associated timing information based on a set of predefined surgical phases; (2) identifying a subset of the set of surgical phases statistically-known to contain PII; and (3) randomly selecting the set of verification video segments from a subset of the set of video portions corresponding to the identified subset of the surgical phases.

In some embodiments, the process performs additional PII removal steps on the anonymized surgical video by first identifying each video portion in the subset of video portions that contains a randomly-selected verification video segment which is again determined to contain PII. Next, for each identified video portion determined to contain PII, the process performs PII removal steps to the identified video portion to de-identify remaining PII within the identified video portion.

In some embodiments, the process identifies the subset of surgical phases statistically-known to contain PII by identifying one or more surgical phases among the set of predefined surgical phases which have high probabilities to contain one or more out-of-body (OOB) events. Note that an OOB event corresponds to a time period when an endoscope is outside of a patient's body during the surgical procedure.

In some embodiments, the time period when the endoscope is outside of a patient's body can include: (1) a time period when the endoscope is temporarily taken out of the patient's body during the surgical procedure; (2) a time period shortly before the endoscope being inserted into the patient's body at the beginning of the surgical procedure; and (3) a time period immediately after the endoscope being taken out of the patient's body at the end of the surgical procedure.

In some embodiments, the process selects the set of verification video segments from the anonymized surgical video by performing a fully-random sampling, i.e., by randomly-selecting the set of verification video segments throughout the anonymized surgical video.

In some embodiments, the process performs additional PII removal steps on the anonymized surgical video by performing a manual PII removal procedure on each segment within the set of verification video segments determined to still contain PII.

In some embodiments, after performing additional PII removal steps on the anonymized surgical video, the process can randomly-sample another set of verification video segments in the updated anonymized surgical video for additional verification.

In some embodiments, the process removes the PII from the surgical video by: (1) detecting one or more forms of personally-identifiable texts within each video image in the surgical video; and (2) when personally-identifiable text is detected within a video image, de-identifying the detected personally-identifiable text by blurring out or otherwise making the detected personally-identifiable text unreadable in the video image.

In some embodiments, the one or more forms of personally-identifiable texts can include: (1) text printed on a surgical tool captured in the set of video images; (2) text displayed inside the OR and accidentally captured during the surgical procedure; and (3) a text box inserted into the surgical video to display surgical procedure-related information.

In another aspect, a system for verifying that an anonymized surgical procedure video is free of personally-identifiable information (PII) is disclosed. This system can include one or more processors and a memory coupled to the one or more processors. The memory stores instructions that, when executed by the one or more processors, cause the system to: (1) receive an anonymized surgical video, wherein the anonymized surgical video was obtained by removing personally-identifiable information (PII) from a raw surgical video of a surgical procedure; (2) select a set of verification video segments from the anonymized surgical video; and (3) determine whether each segment in the set of verification video segments is free of PII. If each verification video segment is determined to be free of PII, the system is further configured to replace the raw surgical video with the anonymized surgical video for storage. Otherwise, the system is further configured to perform additional PII removal steps on the anonymized surgical video to generate an updated anonymized surgical video.

In some embodiments, the system is configured to select the set of verification video segments by performing a strategic random-sampling that includes the steps of: (1) segmenting the anonymized surgical video into a set of video portions including the associated timing information based on a set of predefined surgical phases; (2) identifying a subset of the set of surgical phases statistically-known to contain PII; (3) randomly selecting the set of verification video segments from a subset of the set of video portions corresponding to the identified subset of the surgical phases.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1:
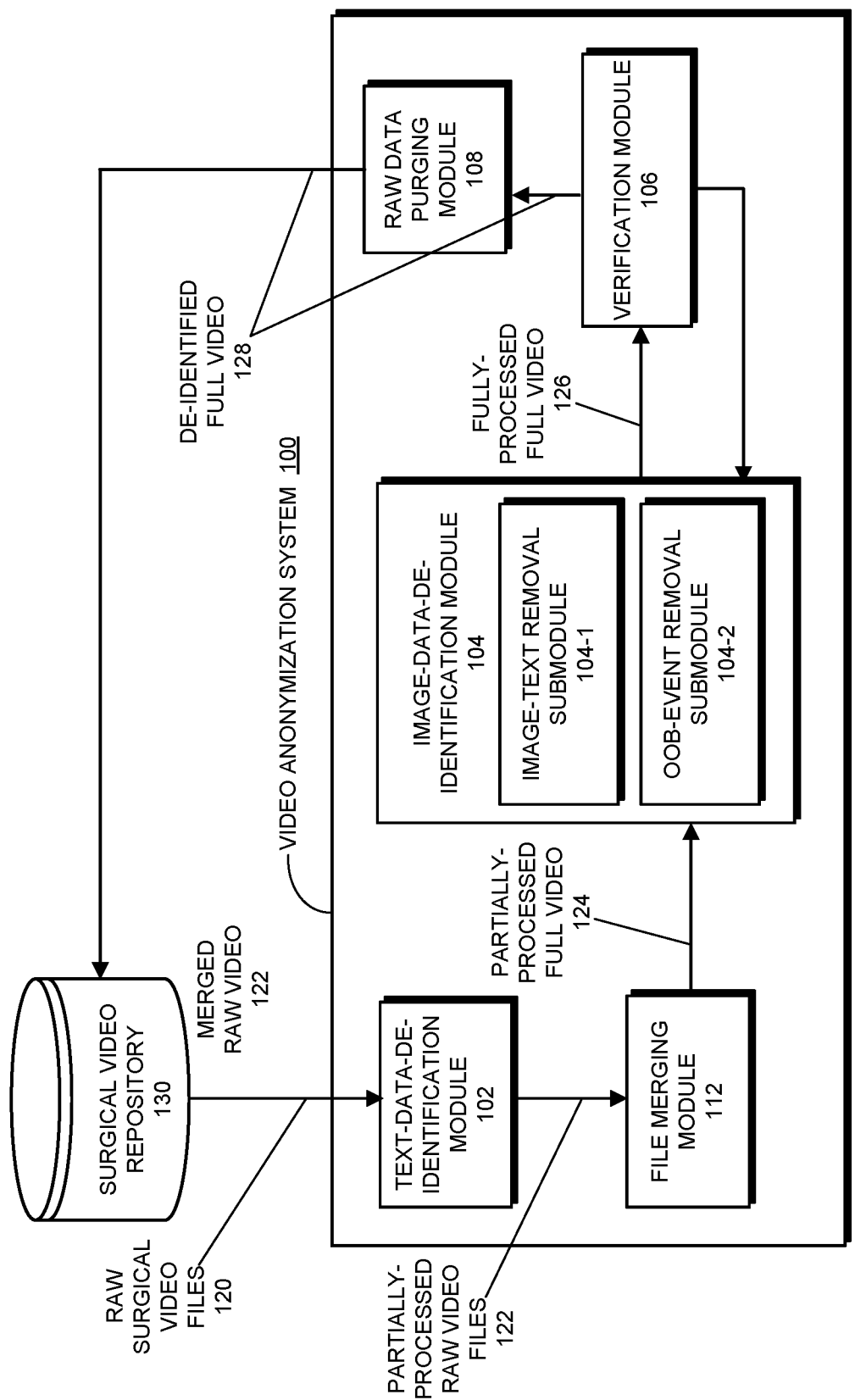
FIG. 1 shows a block diagram of an exemplary raw surgical video anonymization system in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Throughout the specification, the terms "anonymization" and "de-identification" are used interchangeably to mean de-identification of personally-identifiable information. Moreover, the terms "anonymize" and "de-identify" are used interchangeably to mean the action of de-identification of personally-identifiable information. Moreover, the terms "anonymized" and "de-identified" are used interchangeably to mean the result of de-identification of personally-identifiable information.

Raw surgical videos often include all sorts of personally-identifiable information, including both patient identifiable information and surgical staff identifiable information. Patient identifiable information (or "patient data" hereinafter) is any information that can be used to identify the patient, which can include, but are not limited to the name, date of birth (DOB), social security number (SSN), age, sex, address, medical record number (MRN) of the patient, and the time of the surgery. Surgical staff identifiable information (or "staff data" hereinafter) is any information that can be used to identify a given surgical staff member, such as the name of the surgeon performing the procedure. The above-described personally-identifiable information can be in text format. For example, after recording a surgical video, some of the personally-identifiable information can be embedded in the metadata associated with the video files and the file folder which contains the surgical video files. Note that any conventional text-data analysis technique can be used to anonymize or de-identify text-based patient identifiable information associated with recorded raw surgical videos.

In some embodiments, the above-described personally-identifiable information can be in image format and embedded in some of the video frames within a given surgical video. Image-based personally-identifiable information can include text being recorded in various manners during a surgical procedure. For example, text printed on surgical tools used inside patient's body can be recorded during an endoscopic procedure. Such text may identify surgeon's name and the type of the tool be engaged. For example, the video images can capture such text as "Dr. Hogan's scissors" or "Dr. Hogan's staplers" on the corresponding surgical tools. Image-based personally-identifiable information can also include a text box inserted into a recorded procedure video which shows such identifiable information as the name of the surgeon and the name of the hospital. Furthermore, image-based personally-identifiable information can also include patient and/or staff data written on a whiteboard or displayed on a monitor inside an OR room. Note that such information is often accidentally recorded during an out of body event of an endoscope procedure (described in more detail below). Note that personally-identifiable information can also include non-textual information. In particular, non-textual personally-identifiable information can include face images of the patient and/or the surgical staff. Again, such face images can be accidentally recorded during an out of body event of an endoscope procedure. Non-textual personally-identifiable information can also include recorded audio tracks embedded in a raw surgical video.

Note that each raw endoscope video can include a number of out-of-body (OOB) events. An OOB event is generally defined as a time period when the endoscope is taken out of the patient's body for one of various reasons during the surgical procedure while the endoscope camera continues to record, or right before and/or right after the surgical procedure while the endoscope camera is recording. During a surgical procedure, an OOB event can take place for a number of reasons. For example, an OOB event will occur if the endoscope lens has to be cleaned. Note that a number of surgical events can cause the endoscopic view to be partially or entirely blocked to prevent surgeon from viewing the anatomy. These surgical events can include, but are not limited to: (a) endoscope lens is covered with blood (e.g., due to a bleeding complication); (b) fogging of the endoscope lens due to condensation; and (c) endoscope lens is covered with cautery-generated tissue particles, which stick to the lens and eventually block the endoscopic view. In each of the above scenarios, the endoscope camera needs to be taken out of the body so that the endoscope lens can be cleaned to restore visibility or warmed up for condensation removal. After cleaning and/or other necessary treatment, the endoscope camera often needs to be re-calibrated, including performing white-balancing before it can be put back into the patient's body. Note that this lens-cleaning type of OOB event can take a few minutes to complete. Moreover, an initial OOB time/event can exist at the beginning of a surgical procedure if the endoscope camera is turned on prior to being inserted into the patient's body; and a final OOB time/event can exist at the end of a surgical procedure if the endoscope camera remains turned on for a period of time after the completion of the surgical procedure when the endoscope camera has been taken out of the patient's body.

However, each time the endoscope camera is taken out of the patient's body, it is possible that the surgeon unintentionally points the camera to someone in the OR, such as the patient or a surgical staff member including the surgeon him/herself, so that the face images of one or more persons in the OR can be captured in the raw surgical video. Moreover, during an OOB event, it is possible that the surgeon accidentally points the camera at an OR whiteboard which shows personally-identifiable information such as the name and DOB of the patient, the names of the surgical staff, the name of the procedure and the hospital, among others. Both the textual personally-identifiable information and face images in the video images captured during these OOB events have to be anonymized/de-identified.

The disclosed raw surgical video anonymization techniques can be used to detect and anonymize/de-identify each type of the above-described personally-identifiable information, either in forms of textual information embedded in video frames or in forms of face images in video frames. For example, the textual information embedded in video frames can include text/dialog panels/boxes inserted in the video frames, text printed on surgical tools, and textual information on a whiteboard or a monitor inside an OR accidentally captured during an OOB event; whereas face images in video frames can include faces of the patient and surgical staff inside an OR accidentally captured during an OOB event. After processing a given surgical procedure video with the disclosed video anonymization techniques, the given surgical video becomes fully anonymized such that the identity of either the patient or a surgical staff member cannot be identified from the anonymized video images.

FIG. 1 shows a block diagram of an exemplary raw surgical video anonymization system 100 in accordance with some embodiments described herein. As can be seen in FIG. 1, raw surgical video anonymization system 100 (or "video anonymization system 100" hereinafter) includes a text-data-de-identification module 102, a file merging module 112, an image-data-de-identification module 104, a verification module 106, and a raw data purging module 108, which are coupled to each other in the illustrated order.

Generally speaking, file merging module 112 is configured to stitch together a set of video clips/files into a full procedure video; text-data-de-identification module 102 is configured to process a raw surgical video to detect and de-identify text-based personally-identifiable information embedded in file and file-folder identifiers; image-data-de-identification module 104 is configured to process a raw surgical video to detect and de-identify various types of image-based personally-identifiable information embedded in raw video images; verification module 106 is configured to ensure that an anonymized surgical video outputted by image-data-de-identification module 104 is indeed free of any personally-identifiable information; and raw data purging module 108 is configured to permanently remove raw surgical videos and associated file identifiers from a raw surgical video repository and replace the removed raw videos with de-identified videos. We now describe each of the components of video anonymization system 100 in more detail.

As shown in FIG. 1, text-data-de-identification module 102 of video anonymization system 100 is coupled to a surgical video repository 130, which is generally not part of video-anonymization system 100. In some embodiments, surgical video repository 130 is a HIPAA compliant video repository. In some embodiments, surgical video repository 130 can temporarily store raw surgical procedure videos recorded for surgical procedures performed in the ORs, wherein the surgical procedures can include open surgery procedures, endoscopic surgery procedures, or robotic surgery procedures. As such, the raw surgical procedure videos can include various types of raw surgical videos, including but not limited to raw open surgery videos, raw endoscopic surgery videos, and raw robotic surgery videos.

Note that if a full surgical procedure is recorded into a single video file, the video can be a few hours in length (e.g., 2-2.5 hours) and multiple gigabytes in file size (e.g., 4-5 GB). However, hospital IT department often places some restrictions on how big the actual file sizes can be because these recorded raw video files have to be transferred to different storage devices. As a result, a long surgical procedure is typically broken down and recorded as a set of shorter video segments, such as a set of video files of 500-megabyte (MB) per file. For example, a full surgical procedure corresponding to a 4-gigabyte (GB) procedure video will be recorded as eight 500 MB video files instead of a single 4-GB video. However, the original order or some time-sequence information of the set of recorded segments needs to be known in order to reconstruct the full surgical procedure later on, e.g., by file merging module 112.

In the embodiment shown, text-data-de-identification module 102 receives a set of raw surgical video files 120 corresponding to a set of recorded video segments/clips of a full surgical procedure from surgical video repository 130. Text-data-de-identification module 102 is configured to process the received set raw video files to detect text-based personally-identifiable information embedded in file identifiers (e.g., filenames), folder identifiers (e.g., folder names), file properties, and other metadata associated with the set of raw surgical video files 120. Text-data-de-identification module 102 subsequently removes or otherwise de-identifies the detected text-based personally-identifiable information from the corresponding file identifiers, folder identifiers, and other metadata associated with the set of raw video files 120. Text-data-de-identification module 102 then outputs a set of partially-processed raw video files 122. Note that text-data-de-identification module 102 can be implemented with open source text detection and removal tools or based on conventional text detection techniques.

In some embodiments, file merging module 112 receives the set of partially-processed raw video files 122 corresponding to the set of recorded video segments/clips of the full surgical procedure from text-data-de-identification module 102, and subsequently stitches together the set of partially-processed raw video files to recreate a partially-processed full procedure video 124 (or "full procedure video 124"). Note that to be able to merge the set of raw video files 122 into a single video file, the set of raw video files needs to have the same format. Also note that for a surgical procedure comprising a set of raw video segments, the set of video segments would have different file names and is typically stored within a single file folder with a folder name. Unfortunately, different recording devices generally have different naming conventions: e.g., some may name the video segments with identifiers "A, B, C, D, E," etc., and some other may name the video segments with identifiers "1A, 1B 1C, 1D," etc. As such, file merging module 112 should be configured to analyze different naming conventions to determine the right order for the set of received video segments associated with a particular recording device in order to merge these segments back to a proper full-length procedure video. Note that if a given surgical procedure is made up of a single video segment, no file merging would actually occur.

In an alternative embodiment to the one shown FIG. 1, instead of receiving the set of partially-processed raw video files 122 from text-data-de-identification module 102, file merging module 112 can separately receive the set of raw video files 120 from surgical video repository 130, and subsequently merge the set of raw video files to recreate a merged (i.e., full procedure) raw surgical video.

Next, image-data-de-identification module 104 receives the partially-processed full procedure video 124. In some embodiments, image-data-de-identification module 104 is configured to detect various types of image-based personally-identifiable information embedded in the raw video images/frames of full procedure video 124, and subsequently de-identify the detected personally-identifiable information in the corresponding video images/frames. As can be seen in FIG. 1, image-data-de-identification module 104 can include a set of data anonymization submodules, such as an image-text de-identification submodule 104-1 and an OOB-event removal submodule 104-2. More specifically, image-text de-identification submodule 104-1 is configured to detect various personally-identifiable text either being recorded or automatically inserted into the raw video images so that they are a part of the raw video images. For example, recorded text can include text printed on surgical tools used during laparoscopic or endoscopic surgical procedure. Recorded text can also include various text-based information displayed inside an OR but accidentally recorded by an laparoscope or endoscope camera during an OOB event, e.g., text written on a whiteboard inside the OR, text printed on surgical staff's scrubs or uniforms, text displayed on a monitor inside the OR, or other text-bearing objects inside the OR. Personally-identifiable text can also include inserted text such as a standard user interface (UI) text box/panel automatically inserted into a recorded procedure video which shows such identifiable information as the name of the surgeon, and the name of the hospital.

After detecting such personally-identifiable text in one or more video frames of the partially-processed full procedure video 124, image-text de-identification submodule 104-1 can also be configured to automatically blur out or otherwise make the detected text unreadable using other special effects or techniques in the corresponding video frames. In some embodiments, for a detected text box within a video frame which is not considered a part of the surgical video, the entire text box may be blurred out or otherwise edited out. In some other embodiments, the text within a detected text box can be recognized first, and then the recognized text can be separated into sensitive text and the informative text. Next, only the determined sensitive text, such as the name of the surgeon will be blurred out or otherwise edited out, whereas the determined informative text, such as the surgical tool type/name can be left in the video images untouched.

In various embodiments, image-text de-identification submodule 104-1 can include one or more machine-learning models trained to detect and identify various recorded text and text boxes within a given video image, such as text printed on a surgical tool or displayed within a text box. Hence, image-text de-identification submodule 104-1 can use the one or more machine-learning models to automatically identify different types of personally-identifiable text embedded in the video images of partially-processed video 124, and automatically blur out/make unreadable or otherwise de-identify the detected text data in the corresponding video images.

As an example, image-text de-identification submodule 104-1 can include a surgical-tool-text-detection model configured to first detect a surgical tool within a video image with a machine-learning-based tool-detection-and-recognition model. Next, surgical-tool-text-detection model further processes the detected tool image to detect any personally-identifiable text within a boundary of the detected tool image. If such text is detected, image-text de-identification submodule 104-1 is configured to blur out or otherwise make the detected text unreadable.

As another example, image-text de-identification submodule 104-1 can include a text-box detection model configured to detect a standard UI panel or a standard dialog box within video images. In some embodiments, this text-box detection model may be trained based on a set of video images containing inserted text panels. To prepare the training data, properly-sized boxes can be drawn around the text panels within the training images, indicating that the contents inside the text boxes are not part of the surgical video. Next, the text-box detection model can be trained based on these generated text boxes to teach the model to look for such standard UI panels within other video frames which could contain personally-identifiable text that needs be edited out. Note that a single video frame may contain more than one such standard UI panel/text box which should be detected by the model. In some embodiments, the text-box detection model can also learn from the training data the potential locations of the potential UI panels/text boxes within a given video frame to facilitate detecting these standard UI panels/text boxes with higher accuracy and faster speed.

In some embodiments, multiple machine-learning-based image-text detection models can be constructed such that each of the detection models is used to detect a particular type of image-text embedded in the video images. For example, in additional to the above-described text-box detection model, there can be a surgical-tool-text detection model constructed to detect text printed on surgical tools, a whiteboard-text detection model constructed to detect text captured from an OR whiteboard, and a monitor-text detection model constructed to detect text captured from an OR monitor. In various embodiments, the above-described one or more image-text detection models for detecting text embedded in video images can include a regression model, a deep neural network-based model, a support vector machine, a decision tree, a Naive Bayes classifier, a Bayesian network, or a k-nearest neighbors (KNN) model. In some embodiments, each of these machine-learning models is constructed based on a convolutional neural network (CNN) architecture, a recurrent neural network (RNN) architecture, or another form of deep neural network (DNN) architecture.

Referring back to FIG. 1, OOB-event removal submodule 104-2 of data-de-identification module 104 is configured to detect each OOB event within a raw surgical video and subsequently remove the identified OOB segment from the raw surgical video. In some embodiments, OOB-event removal submodule 104-2 can include an OOB event detector which is configured to scan a procedure video to look for OOB events. For example, such an OOB event detector can include an image processing unit configured to detect when the endoscope is being taken out of the patient's body, i.e., the beginning of an OOB event. The image processing unit is also configured to detect when the endoscope is being inserted back into the patient's body, i.e., the end of the OOB event. Hence, the sequence of video frames between the detected beginning and the end of the OOB event corresponds to a detected OOB segment within the full procedure video. In some embodiments, for each detected OOB segment, each video frame in the detected OOB segment can be completely blurred out or otherwise edited out (e.g., replaced with a black screen), so that any personally-identifiable information within an edited video frame, such as all recorded text and inserted text boxes, and non-textual personally-identifiable information such as human faces cannot be identified. Note that generally the video frames associated with each detected OOB segment are only blurred out or otherwise edited out but the actual frames are not cut out from the video, thereby maintaining the original timing information for the detected OOB events.

In various embodiments, OOB-event removal submodule 104-2 can include a machine-learning-based OOB-event detection model trained to detect an OOB segment within a raw surgical video. This OOB-event detection model may be trained based on a set of labeled video segments of a set of actual OOB events extracted from actual surgical procedure videos. The OOB-event detection model can also be trained based on a set of video segments of a set of simulated OOB events extracted from actual procedure videos or training videos. For example, if a training OOB video segment corresponds to a 15-second segment of a procedure video, then all the video frames from the 15-second segment can be labeled with an "OOB" identifier. Next, the OOB-event detection model can be trained based on these labeled video frames to teach the model to detect and identify similar events in raw surgical videos.

As mentioned above, different OOB events may be caused by different reasons, e.g., one may be due to switching from a robotic procedure to a laparoscopic procedure while another can be due to lens cleaning. However, there are strong similarities among different OOB events because they typically all include a beginning phase when the endoscope camera is been taken out of the patient's body and an ending phase when the endoscope camera is been placed back into the patient's body. Hence, a single trained OOB-event detection model may be used by OOB-event removal submodule 104-2 to detect various OOB events within a full procedure video caused by different reasons, and each detected OOB video segment is subsequently blurred out, blacked out, or otherwise de-identified. However, in some embodiments, multiple machine-learning-based OOB-event detection models can be constructed such that each of the OOB-event detection models is used to detect one type of OOB events caused by a particular triggering reason/event.

In various embodiments, the above-described single or multiple OOB-event detection models for detecting OOB segments in full surgical procedure videos can include a regression model, a deep neural network-based model, a support vector machine, a decision tree, a Naive Bayes classifier, a Bayesian network, or a k-nearest neighbors (KNN) model. In some embodiments, each of these machine-learning models is constructed based on a convolutional neural network (CNN) architecture, a recurrent neural network (RNN) architecture, or another form of deep neural network (DNN) architecture.

Note that personally-identifiable information embedded in the raw video images can also include non-textual personally-identifiable information. In particular, non-textual personally-identifiable information can include face images of the patient and/or the surgical staff. For example, such face images can be accidentally recorded during an OOB event. However, any face images captured during an OOB event can be effectively removed using the above-described OOB-event removal submodule 104-2. In some embodiments however, image-data-de-identification module 104 can also include a face-image removal submodule (not shown in FIG. 1) configured to detect faces embedded in raw video images (e.g., by using conventional face detection techniques), and subsequently blur out or otherwise de-identify each detected faces from the corresponding video images. In some embodiments, to de-identify raw video images, image-data-de-identification module 104 can first apply OOB-event removal submodule 104-2 to a raw surgical video to remove OOB events from the raw surgical video. Next, image-data-de-identification module 104 applies the herein-described face-image removal submodule to the processed video images to search for any faces in video frames outside of the detected OOB segments and subsequently blur out any detected face.

While not explicitly shown, video anonymization system 100 can include additional modules for detecting and de-identifying other types of personally-identifiable information within a raw surgical video not described in conjunction with text-data-de-identification module 102 and image-data-de-identification module 104. For example, video anonymization system 100 may also include an audio-data-de-identification module configured to detect and de-identify audio data containing personally-identifiable information, such as surgical staff communications recorded during the surgical procedure. In some embodiment, an audio-data-de-identification module is configured to completely remove all voice tracks embedded in a given raw surgical video.

As can be seen in FIG. 1, image-data-de-identification module 104 outputs a fully-processed full procedure video 126, which is received by verification module 106. In some embodiments, verification module 106 is configured to ensure that a given fully-processed surgical video is indeed free of any personally-identifiable information. In some embodiments, verification module 106 is configured to perform a random sampling of fully-processed surgical video 126, i.e., by randomly selecting a number of video segments within the fully-processed surgical video and verifying that the randomly selected video segments are free of any personally-identifiable information.

In some embodiments, instead of selecting video segments with full randomness for verification, verification module 106 can perform a strategic random sampling to choose a set of video segments from portions of a processed surgical video having higher probability to contain personally-identifiable information for verification. For example, if it can be learned from statistics that during a particular step/phase or steps/phases of a given surgical procedure, the surgeon would often or almost always take the camera out for cleaning or for other reasons, then it becomes more predictable roughly when one or more OOB events might have taken place during a recorded procedure. Hence, instead of randomly sampling the full video to verify the anonymization result of image-data-de-identification module 104, verification module 106 can first determine one or more time periods associated with the one or more particular procedure steps/phases which have high probabilities to contain an OOB event. Verification module 106 subsequently selects a set of video segments within or around the determined high-probability time periods to verify that the selected video segments are free of any personally-identifiable information.

In some embodiments, verification module 106 can collaborate with a surgical-phase segmentation engine, which is configured to segment a surgical procedure video into a set of pre-defined phases, wherein each phase represents a particular stage of the associated surgical procedure that serves a unique and distinguishable purpose in the entire surgical procedure. More detail of the surgical phase segmentation technique based on surgical video analysis has been described in a related patent application having Ser. No. 15/987,782, and filing date May 23, 2018, the content of which is incorporated by reference herein.

More specifically, fully-processed procedure video 126 or even partially-processed procedure video 124 can be first sent to a phase segmentation engine configured to identify different phases for the surgical procedure video. The outputs from the phase segmentation engine include a set of pre-defined phases and the associated timing information with respect to the full procedure video. Combined with the knowledge of which pre-defined phase(s) have high probability to include an OOB event, verification module 106 can then "zoom" into each of the "high OOB probability" phases of fully-processed procedure video 126, and strategically select a set of video segments from these high-probability phases of the fully-processed video for verification that the selected video segments are free of any personally-identifiable information.

In some embodiments, verification module 106 can also reuse the above-described OOB-event-detection model to identify the exact segments of fully-processed procedure video 126 that correspond to the detect OOB events. Each identified OOB video segment is then directly verified (e.g., by a human operator) to determine whether the OOB video segment is free of any personally-identifiable information.

In some embodiments, if verification module 106 determines that a given sampled video segment is not completely free of personally-identifiable information, video anonymization system 100 can be configured to reapply image-data-de-identification module 104 on a portion of fully-processed procedure video 126 containing the problematic video segment in an attempt to de-identify any remaining personally-identifiable information in the portion of the video (shown in FIG. 1 by the arrow going back to module 104 from verification module 106). Alternatively, a manual de-identification process can be used to de-identify any remaining personally-identifiable information within the sampled video segments determined to contain personally-identifiable information. In some embodiments, after reapplying image-data-de-identification module 104 to or performing manual de-identification on the problematic video segments, verification module 106 can be reapplied on the further processed surgical video to perform another pass of the above-described verification operations.

Referring back to FIG. 1, after verification module 106 has verified the anonymization result of fully-processed full procedure video 126, verification module 106 outputs a de-identified surgical video 128 free of any personally-identifiable information, i.e., any patient or surgical staff in the video is completely unidentifiable. Upon receiving de-identified surgical video 128, raw data purging module 108 can be configured to permanently remove any raw and partially-processed video file along with the detected textual-based personally identifiers. For example, raw data purging module 108 can permanently remove raw surgical video files 120, raw surgical video file 122, partially-processed full procedure video file 124 and fully-processed full procedure video file 126.

In some embodiments, after purging the raw and partially-processed surgical videos, raw data purging module 108 is also configured to store de-identified surgical video 128 back into surgical video repository 130. If surgical video repository 130 also stores the original raw surgical video files 120 of de-identified surgical video 128, raw data purging module 108 can be configured to permanently remove any copy of the raw surgical video files 120 from surgical video repository 130. In some embodiments, raw data purging module 108 is also configured to create a database of the de-identified surgical videos. In some embodiments, a database entry in surgical video repository 130 associated with de-identified surgical video 128 can store the filename, along with other statistical data and properties of de-identified surgical video 128 extracted during the above-described video anonymization process. For example, these statistical data and properties can include, but are not limited to the type of the surgical procedure, a full video/video segment identifier, a laparoscopic procedure/robotic procedure identifier, the number of surgeons contributed to the given procedure, the number of OOB events during the procedure, among others.

Next, the de-identified surgical videos stored in surgical video repository 130 can be released to or otherwise made available to clinical experts for various research purposes. For example, the de-identified surgical videos can be released to surgical video data experts who can use the de-identified surgical videos to construct various machine-learning-based analysis tools. More specifically, the de-identified surgical videos can be used to establish machine learning targets in preparation for mining surgical data from surgical videos of a given surgical procedure as described in a related patent application having Ser. No. 15/987,782, and filing date May 23, 2018; to build machine-learning-based surgical tool inventory and tool usage tracking tools as described in a related patent application having Ser. No. 16/129,607, and filing date Sep. 12, 2018; or to build surgical phase segmentation tools also described in the related patent application having Ser. No. 15/987,782, and filing date May 23, 2018, the content of these related patent applications is incorporated by reference herein.

Figure 2:
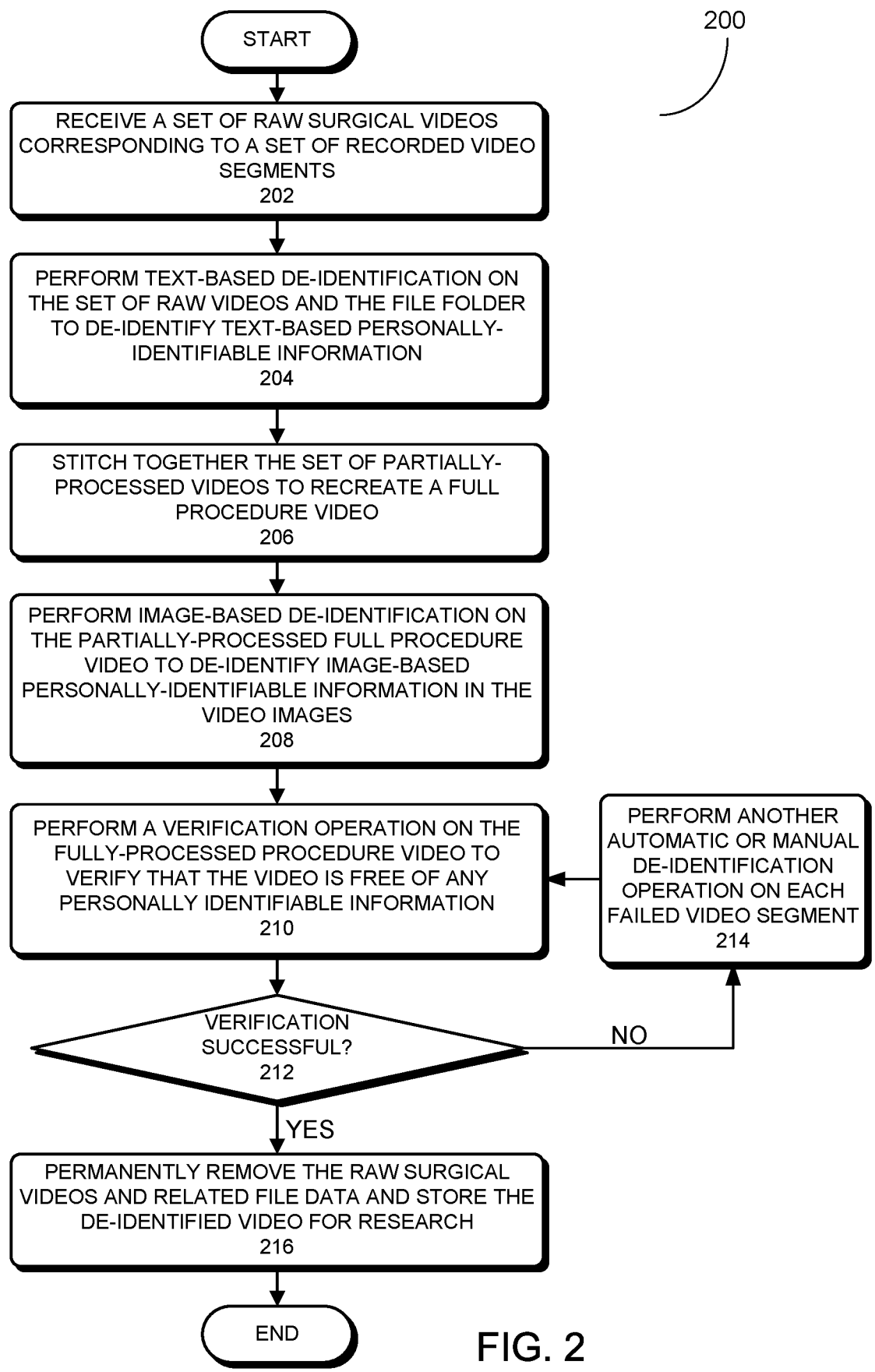
FIG. 2 presents a flowchart illustrating an exemplary process for anonymizing a raw surgical video to de-identify personally-identifiable information embedded in the video images in accordance with some embodiments described herein.

FIG. 2 presents a flowchart illustrating an exemplary process 200 for anonymizing a raw surgical video to de-identify personally-identifiable information embedded in the video images in accordance with some embodiments described herein. In one or more embodiments, one or more of the steps in FIG. 2 may be omitted, repeated, and/or performed in a different order. Accordingly, the specific arrangement of steps shown in FIG. 2 should not be construed as limiting the scope of the technique.

Process 200 may begin by receiving a set of raw surgical videos corresponding to a set of recorded video segments/clips of a full surgical procedure performed in the OR (step 202). As mentioned above, the set of raw surgical videos corresponds to a set of shorter video segments/clips of the full surgical procedure, wherein each of the raw surgical videos can be generated as a result of a maximum file-size constraint, e.g., 500 MB/video. In some embodiments, process 200 can receive the set of raw surgical videos from a HIPAA compliant video repository. In these embodiments, the set of recorded raw surgical videos were first transferred from the OR to the HIPAA compliant repository for temporary storage. In other embodiments, process 200 can receive the set of raw surgical videos directly from a recording device within the OR through a secure network connection, without having to retrieve the stored videos from a HIPAA compliant video repository. Note that when receiving the set of raw surgical video files, process 200 can receive the set of raw video files along with a file folder.

Next, process 200 performs text-based de-identification on the set of received raw surgical videos and the file folder to detect and de-identify text-based personally-identifiable information associated with the raw surgical videos and the associated file folder (step 204). As described-above, the text-based de-identification operation analyzes those text data associated with the raw surgical videos and the file folder (containing the raw surgical videos) that are not embedded in the video images. More specifically, the text-based de-identification operation detects text-based personally-identifiable information embedded in file identifiers (e.g., filenames), folder identifiers (e.g., folder names), file metadata such as file properties, and other metadata associated with the set of raw video files and file folder. As mentioned above, the text-based personally-identifiable information can include both text-based patient data and text-based staff data, and text-based patient data can include, but are not limited to the name, DOB, age, sex, SSN, address, MRN of the patient embedded in the text-based data of the video files and file folder.

Process 200 subsequently removes or otherwise de-identifies the detected text-based personally-identifiable information from the file identifiers, the folder identifiers, and other metadata associated with the set of raw video files and file folder. As mentioned above, process 200 can use open source text detection and removal tools or conventional text detection techniques in step 204. Note that at the end of step 204, the set of raw video files is considered partially-processed: i.e., while the text-based personally-identifiable information has been de-identified, potential personally-identifiable information embedded in the video images has not been de-identified.

Next, process 200 stitches together the set of partially-processed videos to recreate a full procedure video corresponding to the full surgical procedure (step 206). As mentioned above, different recording devices often have different naming conventions. In some embodiment, merging the set of partially-processed video files involves first analyzing the particular naming convention used by the set of video files to determine the correct order for the set of video segments with respect to the full surgical procedure, and subsequently putting together the set of partially-processed videos back to the full procedure video.

Next, process 200 performs image-based de-identification on the partially-processed full procedure video to detect and de-identify image-based personally-identifiable information embedded in the corresponding video images (step 208). As described above, the image-based personally-identifiable information can include various texts either being recorded or automatically inserted into the video frames so that they can be displayed along with the video images. Hence, process 200 can use the above-described image-text de-identification submodule 204-1 to automatically identify different types of personally-identifiable text within raw video images of the full procedure video, and automatically blur out/make unreadable or otherwise de-identify the detected text data embedded in the corresponding video images.

Furthermore, for personally-identifiable information captured during an OOB event, process 200 can use the above-described OOB-event removal submodule 104-2 to automatically detect various OOB segments within the full procedure video, and subsequently blur out, black out, or otherwise de-identify the identified OOB segments from the full procedure video. Moreover, process 200 can use a dedicated face-image removal submodule to search for any face not removed by OOB-event removal submodule 104-2 in video frames outside of the detected OOB segments and blur out each detected face. Note that at the end of step 208, the full procedure video is considered fully-processed.

Next, process 200 performs a verification operation on the fully-processed procedure video to verify that the fully-processed procedure video is free of any personally-identifiable information (step 210). As mentioned above, process 200 can use the above-described verification module 106 to automatically perform either a random sampling of the fully-processed procedure video or a strategic sampling of the fully-processed procedure video.

Next, process 200 determines if the verification operation is successful (step 212). If one or more sampled video segments are found to be not completely free of personally-identifiable information, process 200 can perform either another automatic de-identification operation or a manual de-identification operation on each failed video segment (step 214). After each problematic video segment has been properly processed, the verification operation can be repeated (i.e., process 200 returns to step 210). If the verification operation is determined to be successful at step 212, the video de-identification process is completed. Process 200 then permanently removes the raw surgical videos and related file data from the video repository and stores the de-identified procedure video in place of the removed raw surgical video (step 216).

Note that while the disclosed anonymizing techniques have been described in the scope of anonymizing raw surgical procedure videos, the disclosed techniques can also be used to anonymize still images captured inside an OR to de-identify personally-identifiable information embedded in the still images. Moreover, while some disclosed anonymizing techniques have been described in the scope of anonymizing a set of raw surgical procedure videos corresponding to a long surgical procedure, the disclosed anonymizing techniques can also be applied to a single surgical procedure video to de-identify personally-identifiable information embedded in the single surgical procedure video.

Figure 3:
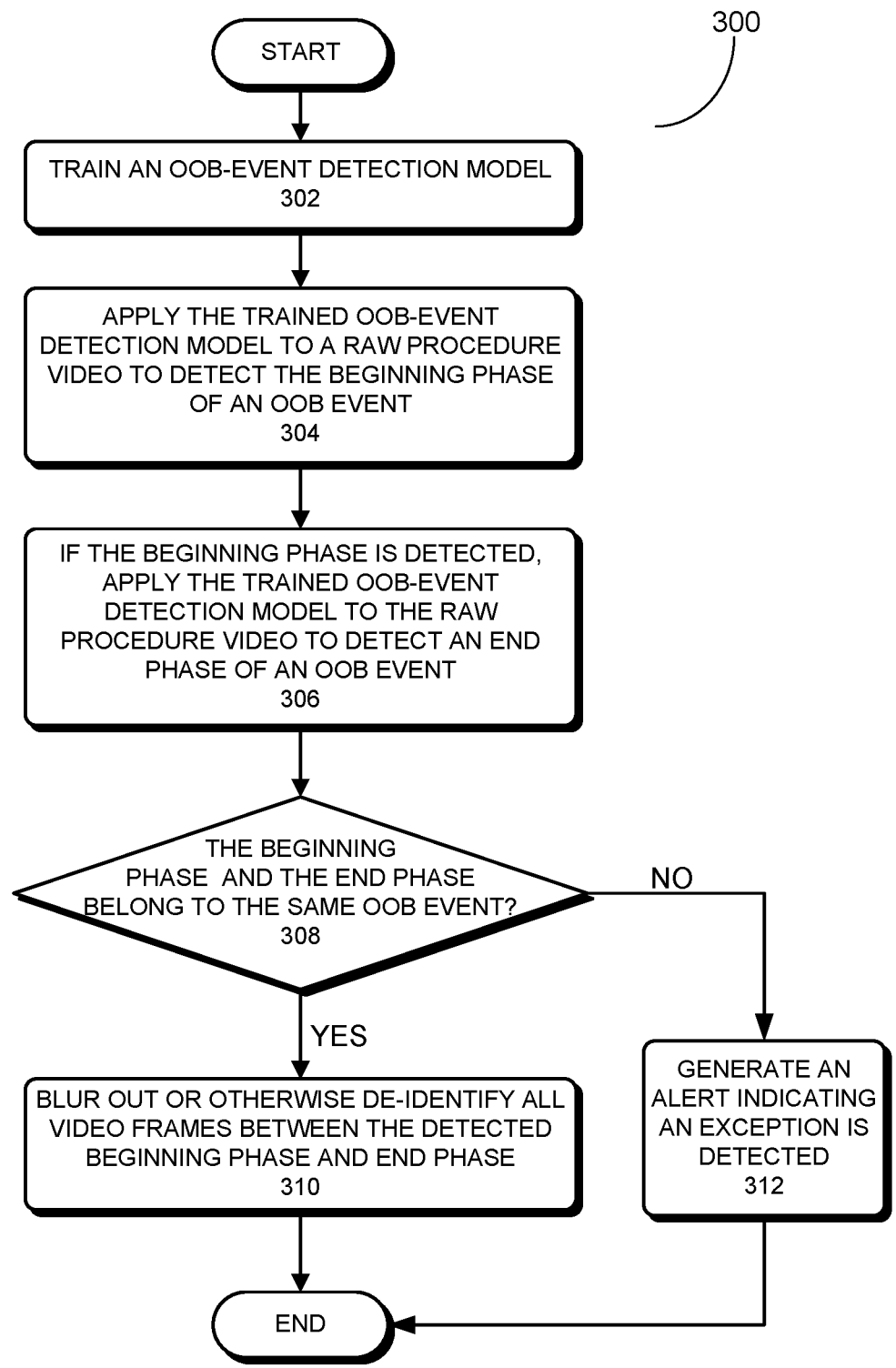
FIG. 3 presents a flowchart illustrating an exemplary process for detecting and removing an out-of-body (OOB) video segment from a raw surgical video to de-identify personally-identifiable information embedded in the associated OOB video images in accordance with some embodiments described herein.

FIG. 3 presents a flowchart illustrating an exemplary process 300 for detecting and removing an OOB video segment from a raw surgical video to de-identify personally-identifiable information embedded in the associated OOB video images in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 may begin by training an OOB-event detection model (step 302). In some embodiment, this OOB-event detection model may be trained based on a set of labeled video segments of a set of actual OOB events extracted from actual surgical procedure videos. For example, if a training OOB video segment corresponds to a 15-second segment of a procedure video, then all the video frames from the 15-second segment can be labeled with an "OOB" identifier. Next, the OOB-event detection model can be trained based on these labeled video frames to teach the model to detect and identify similar events in raw surgical videos. In particular, the OOB-event detection model can be trained to detect the beginning phase of an OOB event, i.e., a sequence of video images corresponding to the event that an endoscope is being taken out of the patient's body; and an ending phase of an OOB event, i.e., a sequence of video images corresponding to the event that the endoscope is being inserted back into the patient's body. The OOB-event detection model is also trained to correlate a detected beginning phase to a detected ending phase to the same OOB event. For example, if the detected ending phase of an OOB event immediately follows the detected beginning phase of an OOB event, and the time interval between the two detections is below a pre-determined threshold, the two detected phases may be considered to belong to the same OOB event.

Process 300 next applies the trained OOB-event detection model to a raw procedure video to detect the beginning phase of an OOB event (step 304). If the beginning phase of an OOB event is detected, process 300 subsequent applies the trained OOB-event detection model to the raw procedure video to detect an ending phase of an OOB event (step 306). Next, process 300 determines if the detected beginning phase and the ending phase belong to the same OOB event (step 308), and if so, process 300 blurs out, blacks out, or otherwise de-identifies all video frames between the detected beginning phase and ending phase of the OOB event (step 310). However, if process 300 determines that the detected beginning phase and the ending phase do not belong to the same OOB event, process 300 may generate an alert indicating an exception is detected (step 312).

Figure 4:
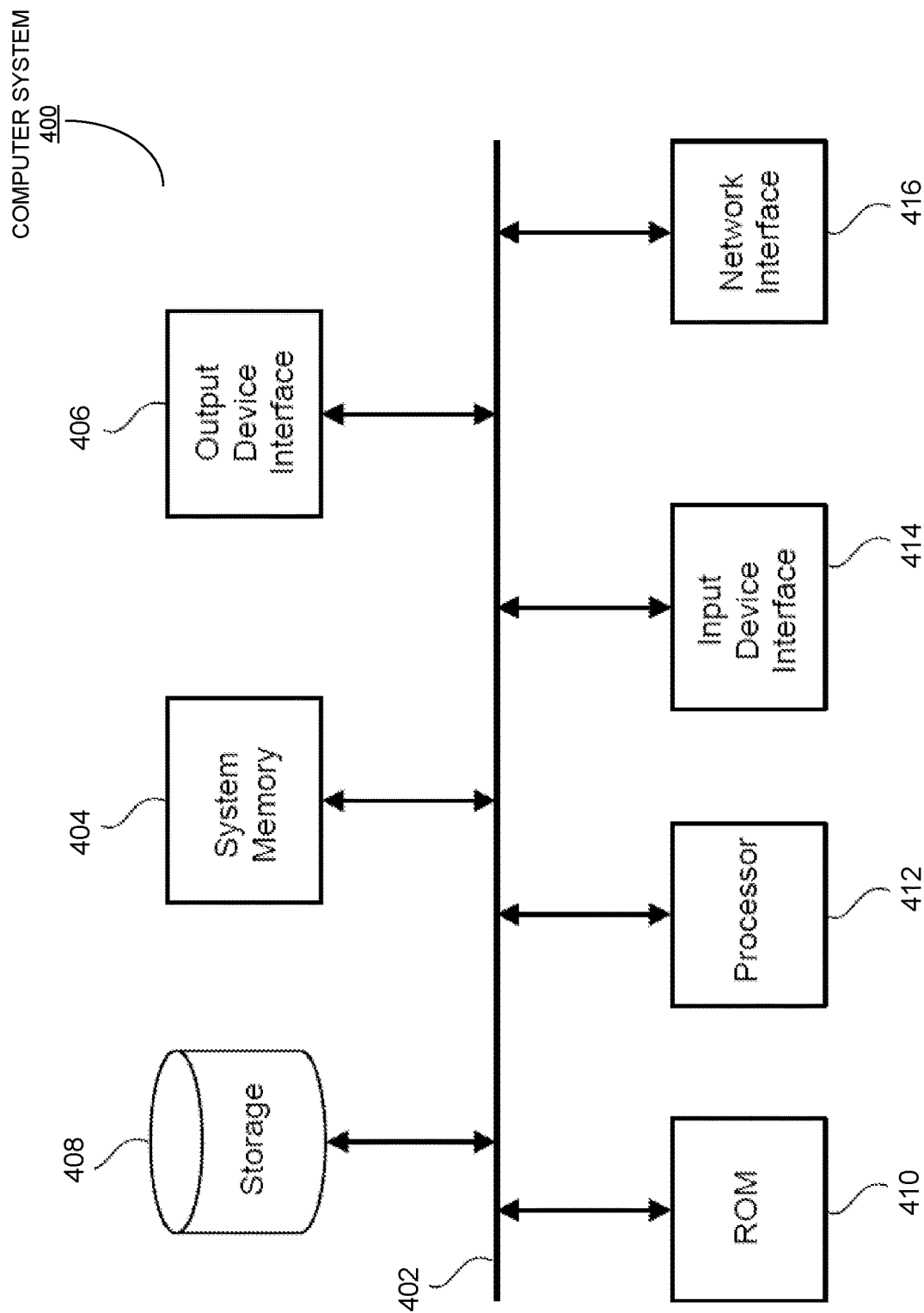
FIG. 4 conceptually illustrates a computer system with which some embodiments of the subject technology can be implemented.

FIG. 4 conceptually illustrates a computer system with which some embodiments of the subject technology can be implemented. Computer system 400 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 400 includes a bus 402, processing unit(s) 412, a system memory 404, a read-only memory (ROM) 410, a permanent storage device 408, an input device interface 414, an output device interface 406, and a network interface 416. In some embodiments, computer system 400 is a part of a robotic surgical system.

Bus 402 collectively represents all system, peripheral, and chipset buses that communicatively connect the numerous internal devices of computer system 400. For instance, bus 402 communicatively connects processing unit(s) 412 with ROM 410, system memory 404, and permanent storage device 408.

From these various memory units, processing unit(s) 412 retrieves instructions to execute and data to process in order to execute various processes described in this patent disclosure, including the above-described processes of anonymizing raw surgical videos to de-identify personally-identifiable information embedded in the corresponding file and folder identifiers, and the corresponding video images in conjunction with FIGS. 1-3. The processing unit(s) 412 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 412 can be a single processor or a multi-core processor in different implementations.

ROM 410 stores static data and instructions that are needed by processing unit(s) 412 and other modules of the computer system. Permanent storage device 408, on the other hand, is a read-and-write memory device. This device is a non-volatile memory unit that stores instructions and data even when computer system 400 is off. Some implementations of the subject disclosure use a mass-storage device (such as a magnetic or optical disk and its corresponding disk drive) as permanent storage device 408.

Other implementations use a removable storage device (such as a floppy disk, flash drive, and its corresponding disk drive) as permanent storage device 408. Like permanent storage device 408, system memory 404 is a read-and-write memory device. However, unlike storage device 408, system memory 404 is a volatile read-and-write memory, such as a random access memory. System memory 404 stores some of the instructions and data that the processor needs at runtime. In some implementations, various processes described in this patent disclosure, including the above-described processes of anonymizing raw surgical videos to de-identify personally-identifiable information embedded in the corresponding file and folder identifiers, and in the corresponding video images in conjunction with FIGS. 1-3, are stored in system memory 404, permanent storage device 408, and/or ROM 410. From these various memory units, processing unit(s) 412 retrieve instructions to execute and data to process in order to execute the processes of some implementations.

Bus 402 also connects to input and output devices 414 and 406. Input devices 414 enable the user to communicate information to and select commands for the computer system. Input devices 414 can include, for example, alphanumeric keyboards and pointing devices (also called "cursor control devices"). Output devices 406 enable, for example, the display of images generated by computer system 400. Output devices 406 can include, for example, printers and display devices, such as cathode ray tubes (CRT) or liquid crystal displays (LCD). Some implementations include devices such as a touchscreen that functions as both input and output devices.

Finally, as shown in FIG. 4, bus 402 also couples computer system 400 to a network (not shown) through a network interface 416. In this manner, the computer can be a part of a network of computers (such as a local area network ("LAN"), a wide area network ("WAN"), an intranet, or a network of networks, such as the Internet. Any or all components of computer system 400 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A method comprising:
receiving surgical video captured by an endoscope that is inserted inside a patient's body during a surgical procedure performed within an operating room (OR);
detecting an out-of-body (OOB) event in a video segment of the surgical video that occurs when the endoscope was taken out of a patient's body while the endoscope is still on by:
detecting, using an image processing algorithm, 1) a field of view of the endoscope that transitions from within the patient's body to outside the patient's body in a first set of video frames of the surgical video as beginning phase of the OOB event and 2) a subsequent field of view of the endoscope that transitions from outside the patient's body to inside the patient's body in a second set of video frames of the surgical video as an ending phase of the OOB event, and
determining that a time interval between the beginning phase and the ending phase is within a threshold period of time; and
responsive to detecting the OOB event, de-identifying personally-identifiable information (PII) embedded within the video segment.

2. The method of claim 1, wherein the video segment comprises a plurality of video frames that make up the OOB event, wherein the PII that is de-identified is within a portion but not all of the plurality of video frames.

3. The method of claim 1, wherein the PII comprises textual information or faces associated with a patient or a surgical staff of the surgical procedure, wherein de-identifying the PII comprises blurring or editing out the textual information or the faces from the video segment.

4. The method of claim 1, wherein the surgical video comprises a plurality of video frames that comprise the first and second sets of video frames and the video segment comprises a sequence of one or more video frames of the plurality of video frames, wherein de-identifying the PII comprises blacking out each video frame of the sequence of one or more video frames that are between the first and second sets of video frames.

5. The method of claim 1 further comprising identifying the video segment of the surgical video based on the surgical procedure, wherein the detecting of the OOB event is performed responsive to identifying the video segment.

6. The method of claim 1, wherein the image processing algorithm is a machine-learning (ML) based OOB-event detection model that is trained to detect OOB events based on a set of labeled video segments of a set of OOB events extracted from actual surgical procedure videos.

7. The method of claim 5, wherein the surgical video comprises one or more de-identified video segments, wherein identifying the video segment comprises:
determining that the video segment has a high-probability of having the OOB event based on the surgical video; and
determining that the video segment is not one of the one or more de-identified video segments.

8. An apparatus comprising:
at least one processor; and
memory having stored therein instructions that when executed by the at least one processor causes the apparatus to:
receive surgical video captured by an endoscope that is inserted inside a patient's body during a surgical procedure performed within an operating room (OR);
detect an out-of-body (OOB) event in a video segment of the surgical video that occurs when the endoscope was taken out of a patient's body while the endoscope is still on by:
detecting, using an image processing algorithm, 1) a field of view of the endoscope that transitions from within the patient's body to outside the patient's body in a first set of video frames of the surgical video as beginning phase of the OOB event and 2) a subsequent field of view of the endoscope that transitions from outside the patient's body to inside the patient's body in a second set of video frames of the surgical video as an ending phase of the OOB event, and
determining that a time interval between the beginning phase and the ending phase is within a threshold period of time; and
responsive to detecting the OOB event, de-identify personally-identifiable information (PII) embedded within the video segment.

9. The apparatus of claim 8, wherein the surgical video comprises a data file with raw video data previously captured by the endoscope during a past surgical procedure performed within the OR.

10. The apparatus of claim 8, wherein the PII comprises textual information or faces associated with a patient or a surgical staff of the surgical procedure, wherein the instructions to de-identify the PII comprises instructions to blur or edit out the textual information or the faces from the video segment.

11. The apparatus of claim 8, wherein the surgical video comprises a plurality of video frames that comprise the first and second sets of video frames and the video segment comprises a sequence of one or more video frames of the plurality of video frames, wherein the instructions to de-identify the PII comprises instructions to black out each video frame of the sequence of one or more video frames that are between the first and second sets of video frames.

12. The apparatus of claim 8, wherein the memory comprises further instructions to identify the video segment of the surgical video based on the surgical procedure, wherein the detecting of the OOB event is performed responsive to an identification of the video segment.

13. The apparatus of claim 8, wherein the image processing algorithm is a machine-learning (ML) based OOB-event detection model that is trained to detect OOB events based on a set of labeled video segments of a set of OOB events extracted from actual surgical procedure videos.

14. The apparatus of claim 12, wherein the surgical video comprises one or more de-identified video segments, wherein the instructions to identify the video segment comprises instructions to:
determine that the video segment has a high-probability of having the OOB event based on the surgical video; and
determine that the video segment is not one of the one or more de-identified video segments.

15. A non-transitory machine-readable medium having instructions that when executed by at least one processor causes the at least one processor to:
> receive surgical video captured by an endoscope that is inserted inside a patient's body during a surgical procedure performed within an operating room (OR);
> detect an out-of-body (OOB) event in a video segment of the surgical video that occurs when the endoscope was taken out of a patient's body while the endoscope is still on by:
> > detecting, using an image processing algorithm, 1) a field of view of the endoscope that transitions from within the patient's body to outside the patient's body in a first set of video frames of the surgical video as beginning phase of the OOB event and 2) a subsequent field of view of the endoscope that transitions from outside the patient's body to inside the patient's body in a second set of video frames of the surgical video as an ending phase of the OOB event, and
> > determining that a time interval between the beginning phase and the ending phase is within a threshold period of time; and
> responsive to detecting the OOB event, de-identify personally-identifiable information (PII) embedded within the video segment.

16. The non-transitory machine-readable medium of claim 15, wherein the PII comprises textual information or faces associated with a patient or a surgical staff of the surgical procedure, wherein the instructions to de-identify the PII comprises instructions to blur or edit out the textual information or the faces from the video segment.

17. The non-transitory machine-readable medium of claim 15, wherein the surgical video comprises a plurality of video frames that include the first and second sets of video frames and the video segment comprises a sequence of one or more video frames of the plurality of video frames, wherein the instructions to de-identify the PII comprises instructions to black out each video frame of the sequence of one or more video frames that are between the first and second sets of video frames.

18. The non-transitory machine-readable medium of claim 15 comprises further instructions to identify the video segment of the surgical video based on the surgical procedure, wherein the detecting of the OOB event is performed responsive to identifying the video segment.

19. The non-transitory machine-readable medium of claim 15, wherein the image processing algorithm is a machine-learning (ML) based OOB-event detection model that is trained to detect OOB events based on a set of labeled video segments of a set of OOB events extracted from actual surgical procedure videos.

20. The non-transitory machine-readable medium of claim 18, wherein the surgical video comprises one or more de-identified video segments, wherein the instructions to identify the video segment comprises instructions to:
> determine that the video segment has a high-probability of having the OOB event based on the surgical video; and
> determine that the video segment is not one of the one or more de-identified video segments.

\* \* \* \* \*